(12) United States Patent
Shanks

(10) Patent No.: US 11,813,476 B1
(45) Date of Patent: Nov. 14, 2023

(54) METHODS OF TREATING THE BRAIN AND NERVOUS SYSTEM USING LIGHT THERAPY

(71) Applicant: Erchonia Corporation, LLC, Melbourne, FL (US)

(72) Inventor: Steven C Shanks, Melbourne, FL (US)

(73) Assignee: Erchonia Corporation, LLC, Melbourne, FL (US)

( * ) Notice: Subject to any disclaimer, the term of this patent is extended or adjusted under 35 U.S.C. 154(b) by 325 days.

(21) Appl. No.: 16/503,000

(22) Filed: Jul. 3, 2019

Related U.S. Application Data

(63) Continuation-in-part of application No. 15/848,514, filed on Dec. 20, 2017, now Pat. No. 11,446,513, and
(Continued)

(51) Int. Cl.
*A61N 5/06* (2006.01)

(52) U.S. Cl.
CPC .......... *A61N 5/0622* (2013.01); *A61N 5/0618* (2013.01); *A61N 2005/0643* (2013.01); *A61N 2005/0663* (2013.01)

(58) Field of Classification Search
CPC ................ A61N 5/0622; A61N 5/0618; A61N 2005/0643; A61N 2005/0663
See application file for complete search history.

(56) References Cited

U.S. PATENT DOCUMENTS

| | | | |
|---|---|---|---|
| 7,947,067 B2 * | 5/2011 | Tucek | A61N 5/0616 606/2 |
| 8,366,756 B2 | 2/2013 | Tucek | |

(Continued)

*Primary Examiner* — Lynsey C Eiseman
*Assistant Examiner* — Jessandra F Hough
(74) *Attorney, Agent, or Firm* — Etherton Law Group, LLC

(57) ABSTRACT

Light energy is applied externally to a patient's head, neck, or both, to treat the brain and nervous system. The light energy stimulates different neurological pathways, reduces inflammation, stimulates mitochondria function in the brain, and increases HRV. The light is applied to the patient on the skull, near the vagus nerve, or a combination thereof. The treatment can be enhanced by activating the cranial nerves while the light is applied.

The wavelengths of the applied light range from ultraviolet to far infrared, and preferably are visible light from about 400-760 nm. In a preferred embodiment the applied light is in the red range and more preferably about of 635 nm±10 nm. The applied light energy is applied with a pulse frequency or frequencies that mimic healthy brain function of alpha, beta, delta, and theta waves such as 8 Hz, 53 Hz, 73 Hz and 101 Hz. The pulse frequencies can be applied singularly, serially, alternately, or simultaneously. This low-level light therapy has an energy dose rate that causes no detectable temperature rise of the treated tissue immediately upon treatment or over time, and no macroscopically visible changes in tissue structure. Advantageously, there is no device or structure between where the laser light exits the laser device and the patient's tissue, The light can be emitted from the same light emitter or from multiple emitters. Preferably the light is laser light and is emitted as a line from a hand-held laser device, and the line is waved manually across a treatment area in a continuous, sweeping manner.

1 Claim, 10 Drawing Sheets

Related U.S. Application Data a continuation-in-part of application No. 15/696,083, filed on Sep. 5, 2017, now abandoned, and a continuation-in-part of application No. 15/604,363, filed on May 24, 2017, now abandoned.

(60) Provisional application No. 62/435,326, filed on Dec. 16, 2016.

(56) References Cited

U.S. PATENT DOCUMENTS

| | | | |
|---|---|---|---|
| 8,409,264 B2 | 4/2013 | Shanks | |
| 8,439,959 B2 | 5/2013 | Tucek | |
| 8,813,756 B1 | 8/2014 | Shanks | |
| 8,814,924 B2 | 8/2014 | Shanks | |
| 8,932,338 B2 | 1/2015 | Lim | |
| 9,061,135 B1 * | 6/2015 | Keller | A61N 5/0601 |
| 9,149,650 B2 | 10/2015 | Shanks | |
| 10,987,521 B1 * | 4/2021 | Chicchi | A61B 5/4076 |
| 2005/0024853 A1 * | 2/2005 | Thomas-Benedict | A61N 5/0619 362/103 |
| 2007/0135870 A1 * | 6/2007 | Shanks | A61N 5/0613 607/89 |
| 2007/0233192 A1 * | 10/2007 | Craig | A61N 1/3611 607/45 |
| 2012/0046716 A1 * | 2/2012 | Dougal | A61N 5/0613 607/91 |
| 2016/0287898 A1 * | 10/2016 | Smith | A61N 5/0622 |
| 2018/0015301 A1 * | 1/2018 | Lim | A61N 5/0622 |

* cited by examiner

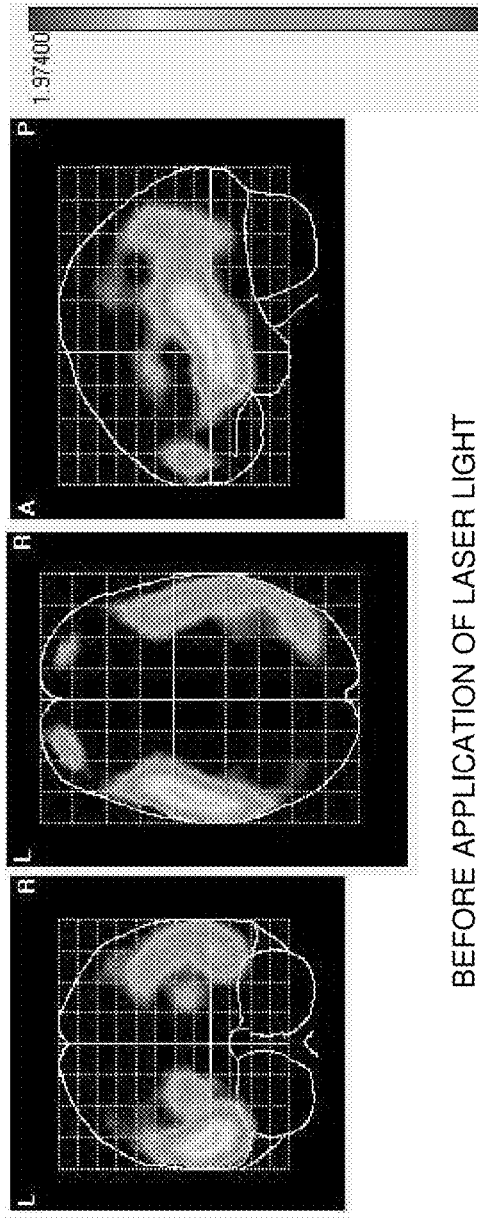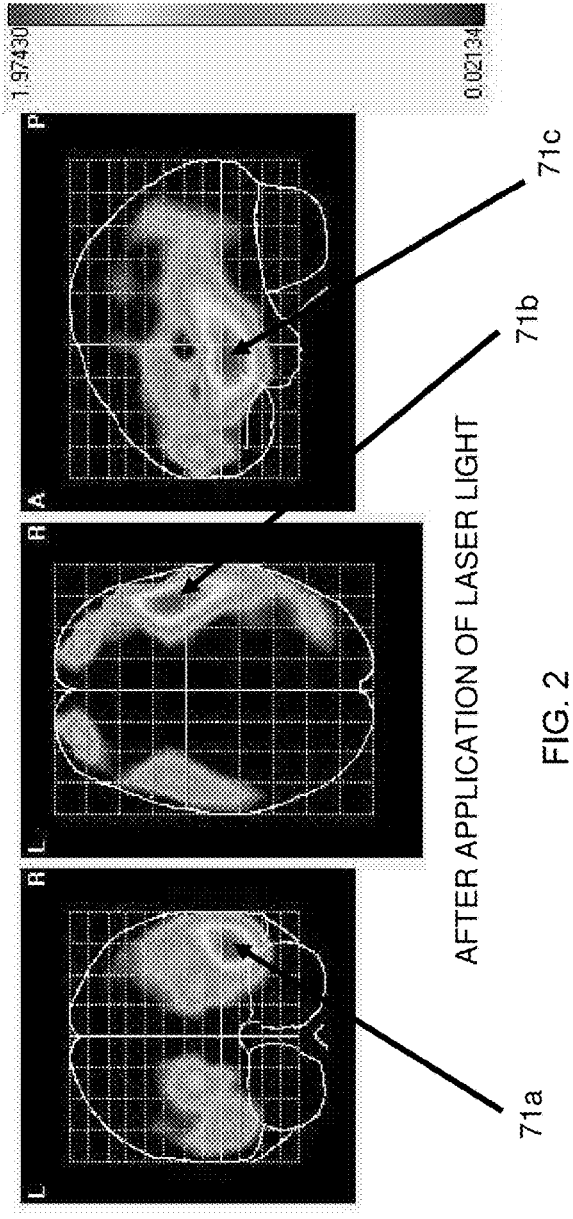
FIG. 2

| Cranial Nerve | Fibers | Structures Innervated | Functions | Brainstem Nucleus |
|---|---|---|---|---|
| I Olfactory | Sensory | Olfactory epithelium (via olfactory bulb) | Olfaction | - |
| II Optic | Sensory | Retina | Vision | - |
| III Oculomotor | Motor | Superior/middle/inferior rectus, inferior oblique, levator palpebrae | Movement of eyeball | Oculomotor nucleus |
| | Parasympathetic | Pupillary constrictor, ciliary muscle of eyeball. Both via the ciliary ganglion | Pupillary constriction and accommodation | Oculomotor nucleus |
| IV Trochlear | Motor | Superior oblique | Movement of eyeball | Trochlear nucleus |
| V Trigeminal | Sensory | Face, scalp, cornea, nasal, and oral cavities, cranial dura mater | General sensation | Trigeminal sensory nucleus |
| | Motor | Muscles of mastication | Opening/closing mouth | Trigeminal sensory nucleus |
| | | Tensor Tympani muscle | Tension of tympanic membrane | Trigeminal sensory nucleus |
| VI Abducens | Motor | Lateral rectus | Movement of eyeball | Abducens nucleus |
| VII Facial | Sensory | Anterior 2/3 of tongue | Taste | Nucleus Solitarius |
| | Motor | Muscles of facial expression | Facial movement | Facial Motor nucleus |
| | Parasympathetic | Salivary and lacrimal glands via submandibular and pterygopalatine ganglia | Salivation and lacrimation | Superior Salivatory Nucleus |
| VIII Vestibulocochlear | Sensory | Cochlea | Hearing | Cochlear Nucleus |
| | | Vestibular apparatus | Proprioception of head, balance | Vestibular nucleus |

FIG. 6

| Cranial Nerve | Fibers | Structures Innervated | Functions | Brainstem Nucleus |
|---|---|---|---|---|
| IX Glossopharyngeal | Sensory | Eustachian tube, middle ear | General sensation | Trigeminal sensory nucleus |
| | | Carotid Body, and sinus | Chemo/baroreception | Nucleus Solitarius |
| | | Pharynx, posterior 1/3 of tongue | Taste | |
| | Motor | Styropharyngeus | Swallowing | |
| | Parasympathetic | Salivary glands via the otic ganglion | Salivation | Inferior Salivatory nucleus |
| X Vagus | Sensory | Pharynx, larynx, oesophagus, external ear | General sensation | Trigeminal sensory nucleus |
| | | Aortic bodies and arch | Chemo/baroreception | Nucleus Solitarius |
| | | Thoracic and abdominal viscera | Visceral sensation | Nucleus Ambiguus |
| | Motor | Soft Palate, larynx, pharynx, upper oesophagus | Speech, swallowing | |
| | Parasympathetic | Cardiovascular, respiratory, and gastrointestinal systems | Control of these systems | Dorsal Motor nucleus of Vagus |
| XI Accessory | Motor | Sternomastoid, trapezius | Movement of head and shoulders | Nucleus Ambiguus, cranial nerves |
| XII Hypoglossal | Motor | Intrinsic and extrinsic muscles of tongue | Movement of tongue | Hypoglossal nucleus |

FIG. 6 cont'd

METHODS OF TREATING THE BRAIN AND NERVOUS SYSTEM USING LIGHT THERAPY

CROSS-REFERENCE TO RELATED APPLICATIONS

This application claims the benefit of U.S. Provisional Application No. 62/435,326 filed Dec. 16, 2016 and is a continuation-in-part of Ser. No. 15/604,363 filed May 24, 2017, Ser. No. 15/696,083 filed Sep. 5, 2017, and Ser. No. 15/848,514 filed Dec. 20, 2017.

FIELD OF INVENTION

This invention relates generally to methods for treating the brain and nervous system. This invention relates more particularly to non-invasive treatments using light therapy.

BACKGROUND

Neurodegenerative diseases occur when nerve cells in the brain or peripheral nervous system lose function over time and may ultimately die. Neurodegenerative disease is a broad category of brain diseases including autism spectrum disorder; Alzheimer's disease; amyotrophic lateral sclerosis ("ALS"); Creutzfeldt-Jakob disease; vascular dementia; Lewy body dementia; fronto-temporal dementia; multi-infarct dementia; vitamin B-12 deficiency syndrome; hypothyroidism; Huntington's disease; Parkinson's disease; normal pressure hydrocephalus; and tauopathies. Many types of neurodegenerative disease are progressive, in which symptoms gradually worsen over time, and can be fatal. Many of these brain diseases involve inflammation and the body's overall inflammatory response.

Neurodegenerative disease is a common problem in older demographics, causing sufferers to have significant cognitive decline with accompanying increase in cost of care and burden on caregivers. With an ageing population, the problem is likely to worsen. The causes of neurodegenerative diseases are not well known and although there are many studies underway for the treatment of the disease and its symptoms, there is no cure. Current available medications treat the symptoms, but often have unwanted side-effects. It would be desirable to treat patients suffering from neurodegenerative diseases in order to minimize the symptoms, stop the progression of the disease, and ideally to cure it.

The brain also suffers from psychiatric disorders, such as depression and anxiety. Current prescription drugs for psychiatric disorders are not generally regarded very highly by the medical profession or by patients, because many of these drugs perform little better than placebos and have unwanted side-effects. It would also be desirable to maintain a healthy brain and delay or prevent depression and anxiety.

Autism spectrum disorder (ASD) is a range of complex neurodevelopment disorders characterized by social impairments, communication difficulties, and restricted, repetitive, and stereotyped patterns of behavior. Autistic disorder, sometimes called autism or classical ASD, is the most severe form of ASD, while other conditions along the spectrum include a milder form known as Asperger syndrome, childhood disintegrative disorder, and pervasive developmental disorder not otherwise specified (PDD-NOS). Evidence suggests that some emotional disorders, such as bipolar disorder, occur more frequently than average in the families of people with ASD.

The cause of ASD is not clearly understood, but it is believed that both genetics and environment likely play a role. A number of genes associated with the disorder have been identified. Studies of people with ASD have found irregularities in several regions of the brain. Other studies suggest people with ASD have abnormal levels of serotonin or other neurotransmitters in the brain, suggesting that ASD could result from the disruption of normal brain development early in fetal development caused by defects in genes that control brain growth and that regulate how brain cells communicate with each other, possibly due to the influence of environmental factors on gene function.

There is no cure and no single best treatment for individuals with autistic disorder. The current standard treatment approach is to customize a customized, highly structured, specialized program or treatment plan incorporating therapies and behavioral interventions targeted toward improving the individual's specific symptoms of autism. Therapies include skill-oriented training sessions to help children develop social and language skills, dietary interventions, and medications to treat anxiety, depression, obsessive-compulsive disorder, or disruptive behaviors associated with autism. The known treatments are complex with often uncertain results, creating a marked challenge for healthcare providers. It would be desirable to treat patients suffering from autism with a relatively simple, non-invasive therapy.

The balance of the sympathetic and parasympathetic divisions of the autonomic nervous system can be evaluated using heart rate variability (HRV). The oscillations of a healthy heart are complex and constantly changing, which enables the cardiovascular system to rapidly adjust to sudden physical and psychological challenges to homeostasis. The human heart rate is variable because of the competition between the branches of the human autonomic nervous system, depending on the stimulus applied. The sympathetic nervous system is the activating branch that initiates "fight or flight," and the parasympathetic nervous system is the deactivating branch that initiates "rest and digest." HRV is a measurement of the time intervals between adjacent heartbeats.

Throughout a typical day, the human body is exposed to various situations that require each system to be turned on and off. The faster the systems can be switched, the more quickly a body adapts to its surroundings. High HRV means a body is highly responsive to its environment. It can quickly shift its energy from "fight or flight" to "rest and digest" to easily match its surroundings. High HRV is related to shorter stress responses in hormonal, cardiac and immune (inflammatory) markers. Low HRV means that either the sympathetic or parasympathetic system is inhibiting the other, meaning the ability to respond to the inhibited branch's inputs is reduced. Low HRV usually means a person is under high stress.

The vagus nerve is the 10th cranial nerve, descending from the brain stem and enabling parasympathetic control of the heart, lungs, and digestive tract. The vagus nerve supplies motor parasympathetic fibers to all the organs (except the adrenal glands), from the neck down to the second segment of the transverse colon. The vagus also controls a few skeletal muscles. The vagus nerve is commonly referred to in the singular, but is actually a pair of nerves, namely the right and left vagus nerves. Vagus nerve activity is very strongly correlated with heart rate variability, so an increase in the HRV indicates increased vagus nerve activity. The vagus nerve inhibits oxidative stress, inflammation and sympathetic activity and associated hypoxia.

Cardiovascular diseases, cancer, and chronic obstructive pulmonary disease share three important pathophysiological contributing factors, namely oxidative stress, inflammation, and excessive sympathetic nerve activity. Recent studies, including one by Gidron et al, J. Clin. Med. 2018, 7, 371, have shown that higher vagus nerve activity predicts and may reduce the risk of non-communicable chronic diseases such as cardiovascular disease, cancer, and chronic obstructive pulmonary disease. It would be desirable to increase vagus nerve activity, as measure by increase HRV to modulate these diseases and others.

The misuse of and addiction to opioids, including prescription pain relievers, heroin, and synthetic opioids such as fentanyl, is a serious national crisis affecting public health and social and economic welfare. In 2016, 11.5 million people misused prescription opioids, with over 40,000 dying from opioid overdose, averaging 116 deaths per day. The Centers for Disease Control and Prevention estimates the annual "economic burden" of prescription opioid misuse in the U.S. to be $78.5 billion, considering the costs of healthcare, lost productivity, addiction treatment, and criminal justice involvement.

Opioid use disorder (OUD) is a chronic disorder with relapse based on both desire for reinforcement (craving) and avoidance of withdrawal and its concomitant pain. Over 2 million Americans had an opioid use disorder in 2016. Among the abused substances, opiates including illicit heroin and prescription opiates are one of the most frequently abused and powerfully dependent drugs. OUD has been associated with severe and dire global and societal consequences. The social burden due to OUD is tremendous but current pharmacological treatments of opioid-related conditions and psychological therapies are still insufficient to reduce the high relapse rate.

OUD is characterized as the compulsion of drug-seeking and drug-taking behaviors despite of harmful consequences, and it encircles a relapsing cycle of intoxication, binging, withdrawal and craving during abstinence (Goldstein and Volkow, 2011). It becomes the notion that the loss of control over drug consumption involves disruption of the reward mesocorticolimbic (MCL) circuits. However, how different substances of abuse manipulate particular brain regions within the circuits and to what extend the affected regions are related to certain cognition and behaviors need further elucidation.

Neuroimaging findings and clinical implications have provided convincing evidence that chronic opiate abuse affects the prefrontal cortex, temporal insula and thalamus, nucleus accumbens, amygdala, and sensorimotor cortices. It would be desirable to treat patients with OUD to contribute to change both anatomic connectivity in the brain and functional connectivity, leading to the reward mesocorticolimbic and other brain circuits. The final result will be a striking lessening of the loss of control over drug consumption in addicted subjects.

Low-level laser therapy ("LLLT") has been shown through numerous clinical studies and regulatory clearances to be a safe and effective, simple, non-invasive and side-effect free alternative to medication and surgical procedures for the reduction of symptoms in a variety of conditions. LLLT reduces edema, improves wound healing, and relieves pain of various etiologies. It is also used in the treatment and repair of injured muscles and tendons. Application of LLLT has been shown to have the potential to alter cellular metabolism to produce a beneficial clinical effect. For example, when hypoxic or otherwise impaired cells are irradiated with LLLT, mitochondrial adenosine tri-phosphate (ATP) production increases and nitric oxide is released. When exposed to near-infrared photons, cytochrome-C oxidase (CCO) releases nitric oxide which diffuses out the cell, increasing local blood flow and vasodilation, effecting a brief burst of reactive oxygen species (ROS) in the neuron cell. This in turn activates numerous signaling pathways that activate redox-sensitive genes and related transcription factors.

Based on its ability to modulate cellular metabolism and alter the transcription factors responsible for gene expression, LLLT has been found to alter gene expression, cellular proliferation, intra-cellular pH balance, mitochondrial membrane potential, generation of transient reactive oxygen species and calcium ion level, proton gradient and consumption of oxygen. LLLT stimulation of the mitochondria via low-energy light has been shown to provoke a dynamic shift in the function of an individual cell. Laser therapy has been shown to stimulate cell regeneration and later gene expression.

Experts in LLLT have long stated that the proper wavelength of light must be used to trigger the desired photobiomodulation. It is a long-held belief by experts in the field that only long, near infrared wavelengths can penetrate deep enough into a patient's tissue or bone to affect cellular behavior, and that shorter wavelengths cannot do so. For example, at least one study has shown that red light does not penetrate a patient's skull. This has led the medical and research communities to believe that the brain cannot be successfully treated with LLLT.

Electrophysiology is the study of the electrical properties of biological cells and tissues. It involves measurements of voltage changes or electric current on a wide variety of scales from single ion channel proteins to whole organs like the heart. In neuroscience, it includes measurements of the electrical activity of neurons and, in particular, action potential activity. Recordings of large-scale electric signals from the nervous system, such as electroencephalography, may also be referred to as electrophysiological recordings. They are useful for electrodiagnosis and monitoring. For example, electroencephalography is commonly used to diagnose brain diseases such as epilepsy.

To determine the location of the brain activity with a resolution greater than what is provided by scalp electroencephalography, neurosurgeons may implant electrodes or insert penetrating depth electrodes under the dura mater, using either a craniotomy or a burr hole. The recording of these sub-dural signals is referred to as intracranial electroencephalography. The signal recorded from intracranial electroencephalography is on a finer scale of activity than the brain activity recorded from scalp electroencephalography. Low voltage, high frequency components that cannot be seen easily (or at all) in scalp electroencephalography can be seen clearly in intracranial electroencephalography. Penetrating microelectrodes are also used to determine the location of brain activity. Quantitative electric tomography is another technique to determine the location of brain activity which combines anatomical information of the brain by MRI with electroencephalography patterns, to estimate the location of the electrical activity within the brain.

While electroencephalography measures the brain's electrical activity directly, other methods measure the electrical activity indirectly. For example, single-photon emission computed tomography (SPECT) and functional magnetic resonance imaging (fMRI) record changes in brain blood flow, which is directly correlated to brain activity. Positron emission tomography (PET) and near-infrared spectroscopy (NIRS) measure metabolic activity in the brain, which are also directly correlated to brain activity.

It is an object of this invention to apply light energy to treat the brain and nervous system. It is an object of this invention to apply light energy to a patient to treat brain and neurological disorders. It is another object of this invention to provide a non-invasive method of activating portions of a healthy brain, thereby maintaining a healthy brain, delaying the onset of brain diseases and disorders, or preventing them entirely. Another object of the methods herein is to increase HRV. It is yet another object to treat opioid addiction.

SUMMARY OF THE INVENTION

Light energy is applied externally to a patient's head, neck, or both, to treat the brain and nervous system. The light energy stimulates different neurological pathways, reduces inflammation, stimulates mitochondria function in the brain, and increases HRV. The light is applied to the patient on the skull, near the vagus nerve, or a combination thereof. The treatment can be enhanced by activating the cranial nerves while the light is applied.

The wavelengths of the applied light range from ultraviolet to far infrared, and preferably are visible light from about 400-760 nm. In a preferred embodiment the applied light is in the red range and more preferably about of 635 nm±10 nm. The applied light energy is applied with a pulse frequency or frequencies that mimic healthy brain function of alpha, beta, delta, and theta waves such as 8 Hz, 53 Hz, 73 Hz and 101 Hz. The pulse frequencies can be applied singularly, serially, alternately, or simultaneously. This low-level light therapy has an energy dose rate that causes no detectable temperature rise of the treated tissue immediately upon treatment or over time, and no macroscopically visible changes in tissue structure. Advantageously, there is no device or structure between where the laser light exits the laser device and the patient's tissue, The light can be emitted from the same light emitter or from multiple emitters. Preferably the light is laser light and is emitted as a line from a hand-held laser device, and the line is waved manually across a treatment area in a continuous, sweeping manner.

BRIEF DESCRIPTION OF THE DRAWINGS

FIG. 2 shows QEEGT images within the gamma band of a healthy brain before and after the application of laser energy.

FIG. 6 is a prior-art table of cranial nerves.

DETAILED DESCRIPTION OF THE INVENTION

Figure 1:
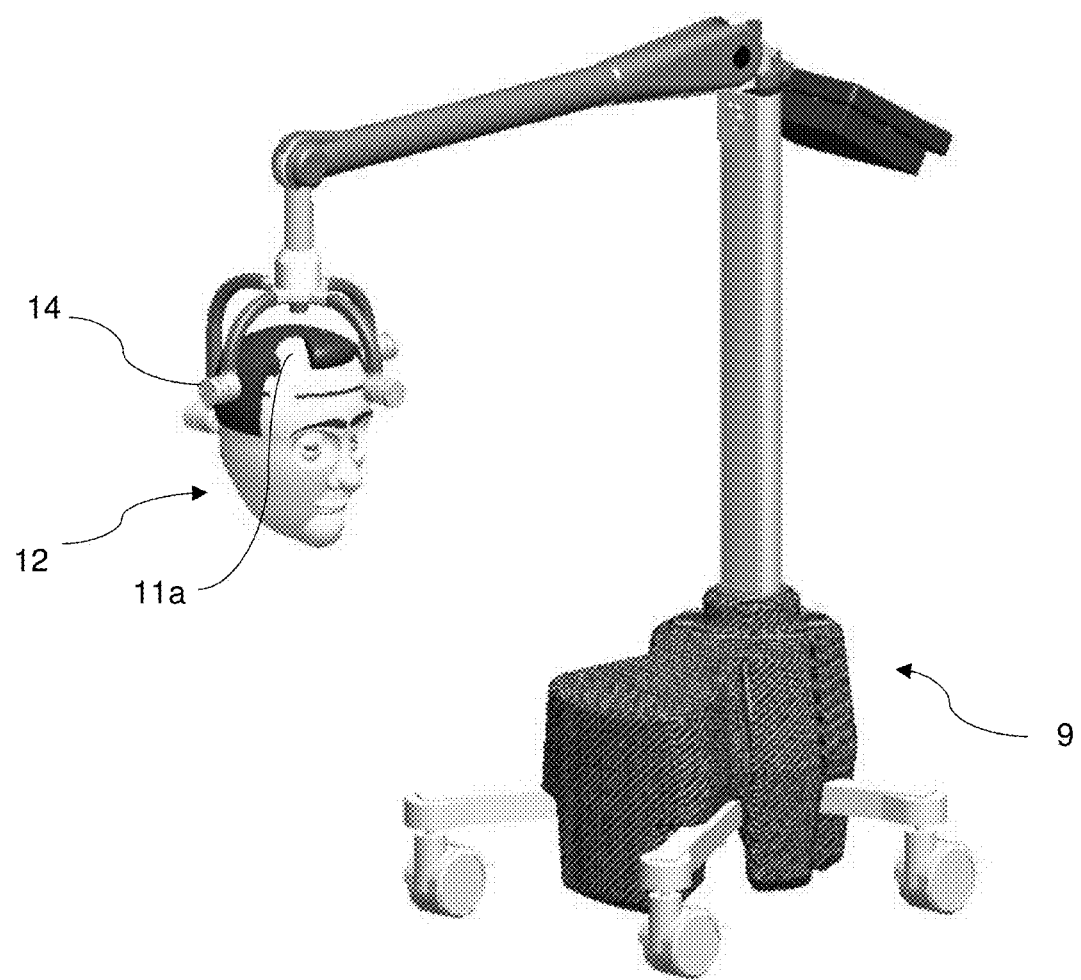
FIG. 1 illustrates a portable, floor-supported light-emitting device for treating a patient's head.
Figure 3:
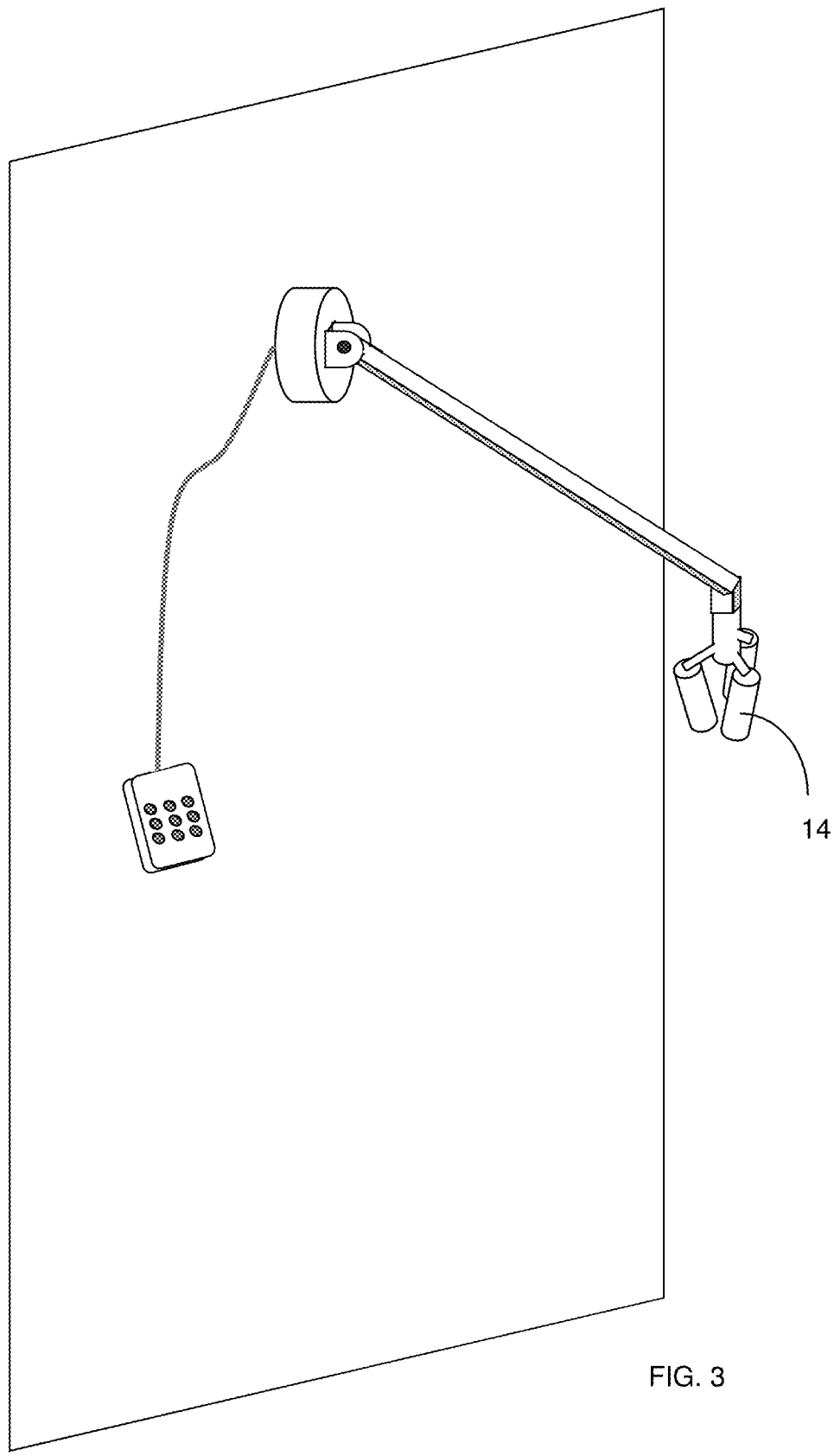
FIG. 3 illustrates a wall mounted light-emitting device for treating a patient's head.

This invention is methods for treating the brain and nervous system by applying light therapy to a patient. There are a number of variables in light therapy, including the wavelength of the light, the power of the light source, the area impinged by the light, the shape of the beam spot when the light impinges the treated area, the pulse frequency, the intensity or fluence of the light energy, and the treatment duration. The success of each therapy depends on the relationship and combination of these variables with the tissue characteristics of the specific patient and desired outcome. For example, as disclosed in more detail below, Alzheimer's disease may be treated with one regimen utilizing a given power, wavelength, pulse frequency and treatment duration, whereas autism may be treated with a regimen utilizing a different power, wavelength, pulse frequency and treatment duration, and either regimen may be further adjusted for a given patient depending on that patient's size, weight, age, and stage of the disease. Some regimens treat healthy brains to prevent brain an neurological disorders.

The wavelengths of the applied light range from ultraviolet to far infrared. Preferably the wavelengths of the light that are applied range from about 400-760 nm nominal, with the desired wavelength within the spread from nominal. However, in other embodiments light having wavelengths above 400 nm and below infrared are used. In some embodiments multiple wavelengths are used, either in series, alternately, or simultaneously. The light can be from any source including light-emitting diodes, hard-wired lasers, or laser diodes, but preferably is from a semiconductor laser diode such as Gallium Aluminum Arsenide (GaAlAs) laser diodes, emitting red laser light at 635 nm nominal. Commercial semiconductor laser diodes have a spread of ±10 nm from nominal so the light applied is within the spread from nominal. FIGS. 1, 3, 8 and 9 illustrate laser devices, each containing at least one laser diode.

The applied light is low-level, often less than 7.5 mW and typically from emitters of less than 1 W. For example, 1 mW, 3 mW, 5 mW, and 7.5 mW of power may be used. In some embodiments, two emitters at 7.5 mW each are used, for a total of 15 mW. This low-level light therapy has an energy dose rate that causes no immediate or long term detectable temperature rise of the treated tissue and no macroscopically visible changes in tissue structure. Consequently, the tissue impinged by the light, hair on the patient, the skull, the brain and nerve tissue are not heated and are not damaged.

The applied light energy is applied with a pulse frequency or frequencies from 0 to 100,000 Hz. In some embodiments the light energy is applied at a pulse frequency or frequencies of brain waves emanating from a healthy brain, as measured by electroencephalography. Brain waves are neural oscillations in a rhythmic or repetitive neural activity that includes the following:

| Wave Type | Approximate Frequency Range in Humans | Main Source Location on the Human Brain |
|---|---|---|
| Delta | 0.5 to 3 Hz 0.5-4 | thalamus or cortex |
| Theta | 3 to 8 Hz | hippocampus |
| Alpha | 8-12.5 Hz | occipital lobe |
| Mu | 7.5-12.5 (and primarily 9-11) Hz | motor cortex |

-continued

| Wave Type | Approximate Frequency Range in Humans | Main Source Location on the Human Brain |
|---|---|---|
| Beta | 12.5 to 38 Hz | posterior brain |
| Gamma | 38 to 100 Hz | all areas of brain |

Other types of oscillatory activity are found in a healthy central nervous system, and light therapy may be applied at a pulse frequency that mimics that oscillatory activity. Multiple pulse frequencies can be applied singularly, serially, alternately, or simultaneously. In one embodiment, the light therapy is applied using several light sources, each having a different frequency.

Light is applied to the patient's head 11. The light may be applied to a patient's shaved skull 11a or through the patient's hair. Because the light energy is low level, there is no need for an intervening device or structure used between where the laser light exits the laser device and the patient to alter, dissipate, or otherwise affect the transmission of the light energy to the patient or affect the temperature of the treated surface, the treated tissue, tissue within the treatment area, around the treatment area, or any intervening or targeted tissue within the patient's body.

Typically the patient is treated while the patient is vertical or nearly vertical, as opposed to prone or supine, so that all regions of the skull and brain stem can be treated without moving the patient. Usually the patient is seated in a chair. The patient can be awake, sedated, or asleep.

Figure 4:
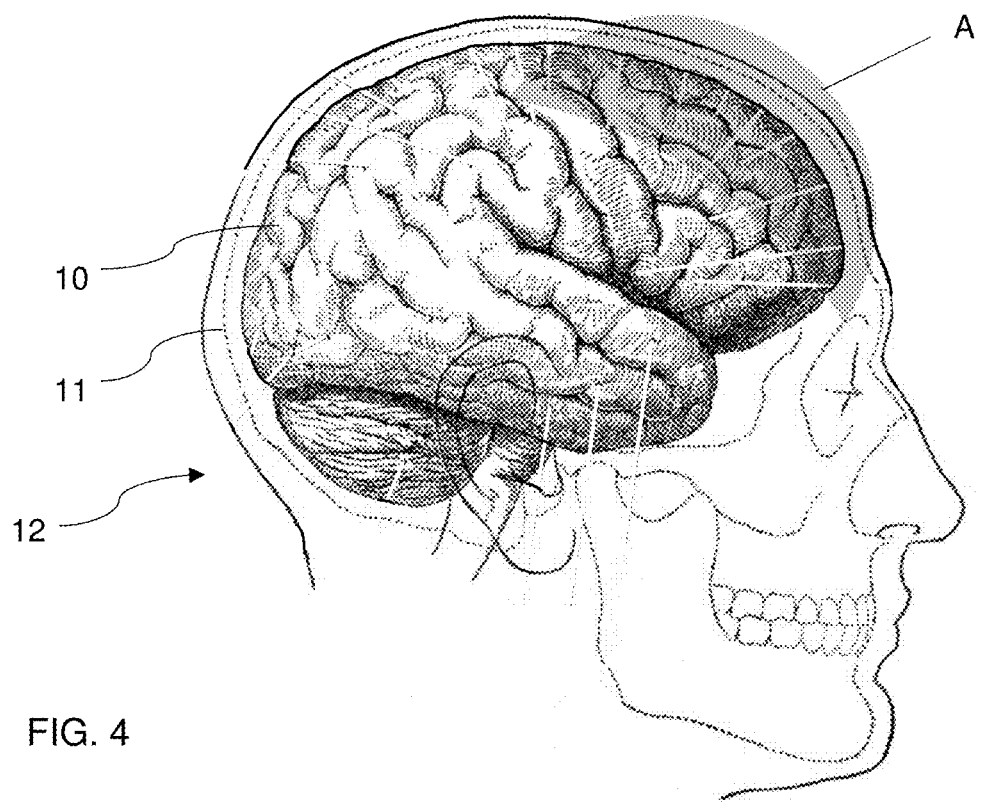
FIG. 4 is a schematic illustration of a brain inside a patient's skull.
Figure 5:
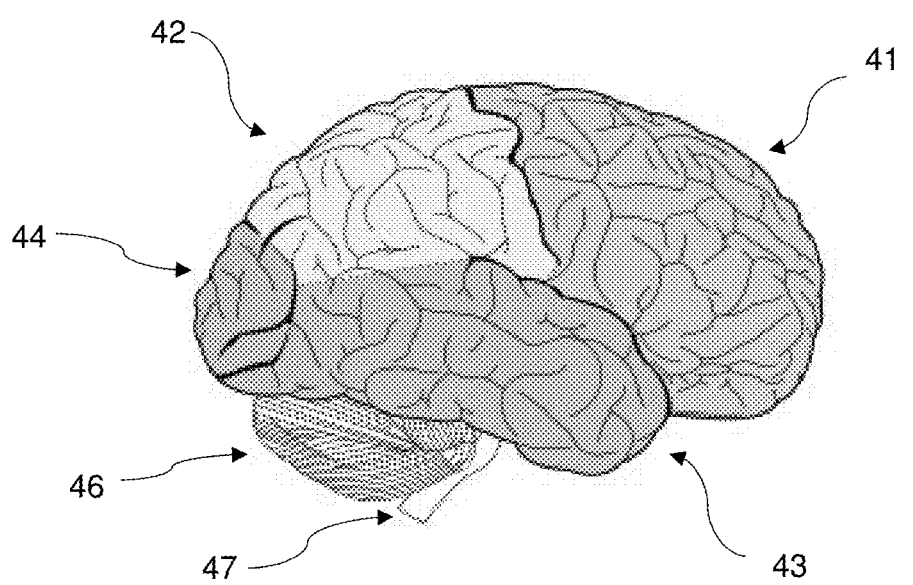
FIG. 5 is a schematic illustration of a brain.
Figure 7:
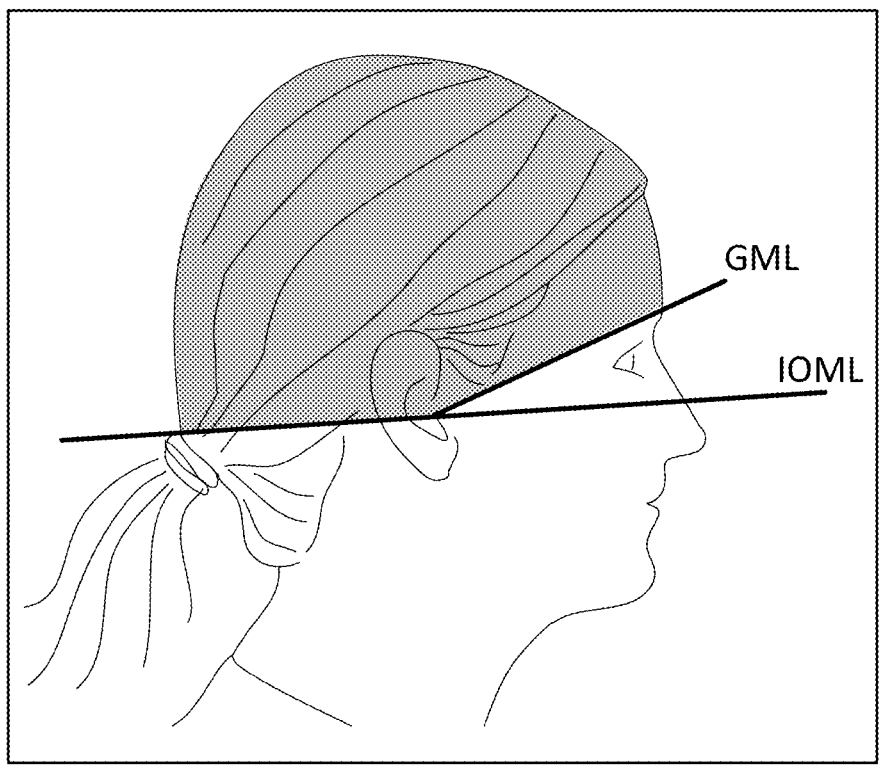
FIG. 7 is a schematic illustration of the area of the skull defined by the glabellomeatal (GML) and infraorbitomeatal (IOML) lines.
Figure 8:
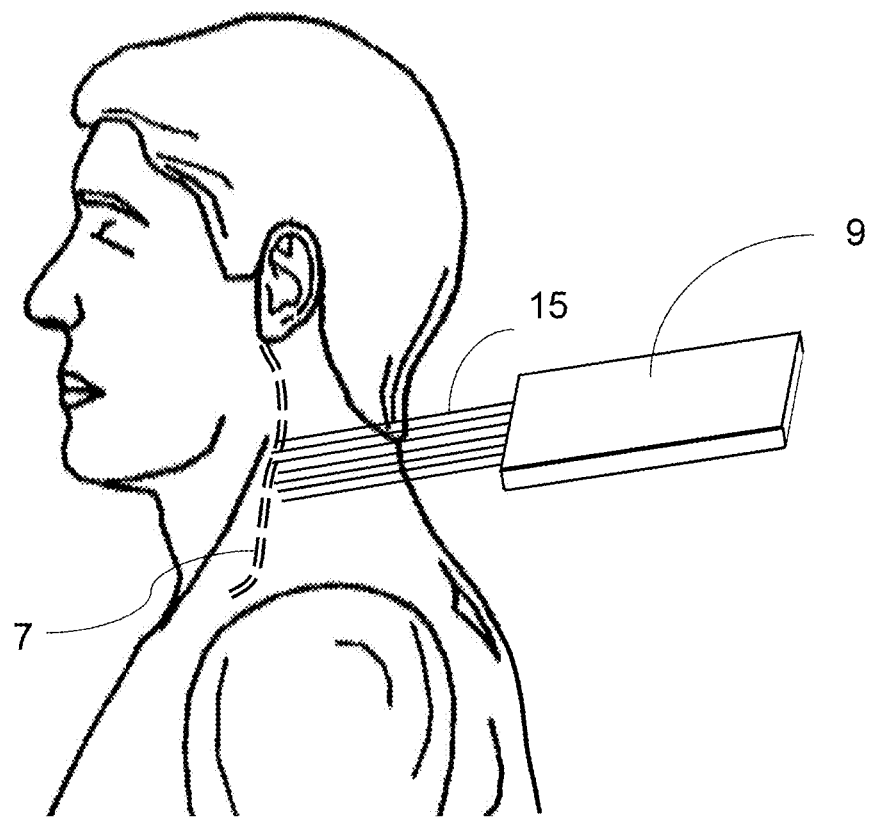
FIG. 8 illustrates laser energy applied by a laser device to the left side of a patient's neck.
Figure 9:
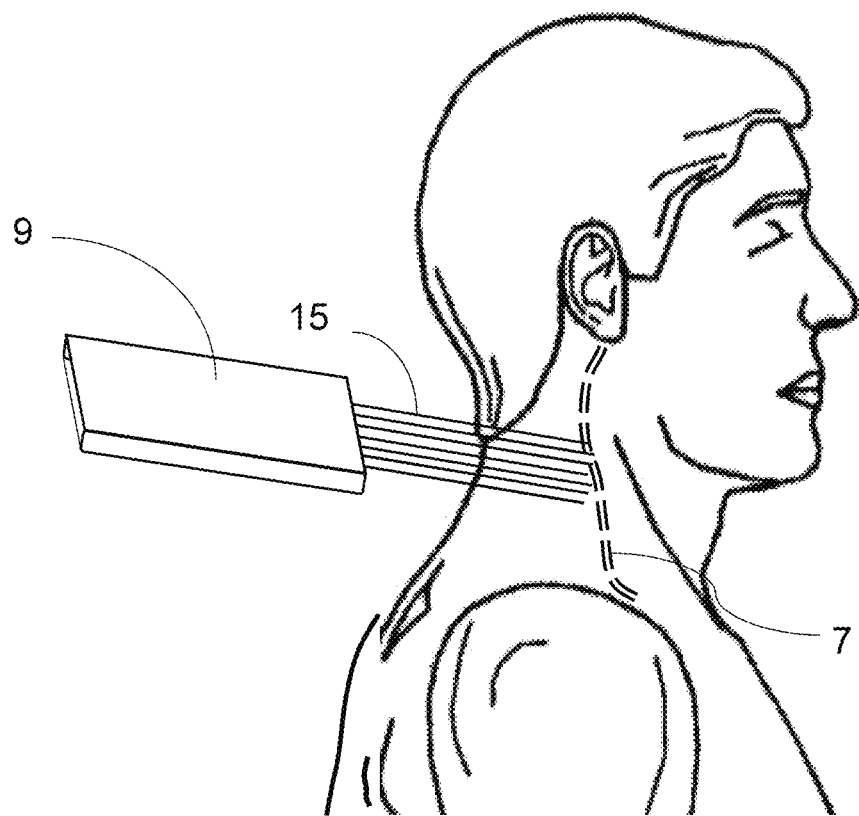
FIG. 9 illustrates laser energy applied by a laser device to the right side of a patient's neck.

The method is non-invasive. The light is applied to the skull or nerves near the area of the brain or cranial nerves (or both) that is malfunctioning or associated with the source of the malady to be treated, if the area is known. As used herein, light applied "near the" area on the head means light applied to the scalp at a position mapped to the area of the brain to be treated, such as the frontal 41, parietal 42, temporal 43, and occipital 44 lobes; the cortex; cerebellum; the brain stem or base of the brain; or where one or more cranial nerves enters the brain. See FIG. 5. For example, if the light is to be applied "near the frontal lobes," it will be applied to the scalp above the frontal cortex, as indicated generally by area A in FIG. 4, which is also above the glabellomeatal and infraorbitomeatal lines, as shown in FIG. 7 and as described in more detail below. In another example, if the light is to be applied "near the area" of the basal ganglia, which is in the center of the brain, the light will be applied to the scalp all around the head from about the ear lobes up to the top of the head. The treatment can be enhanced by activating the cranial nerves while the light is applied. FIG. 6 is a table of the cranial nerves and their functions. A cranial nerve is activated by having the patient to execute the function indicated the table of FIG. 6. For example, to activate the olfactory nerve, the patient would be given something with an odor or scent to smell. Similarly, to activate the trochlear nerve, the patient would move his eyeballs.

The methods herein may be used as a non-invasive method of activating portions of a healthy brain, thereby maintaining a healthy brain, delaying the onset of cognitive decline, brain diseases and disorders, or preventing them entirely. A healthy brain, as used herein, means a brain that shows no measurable signs or symptoms of cognitive decline, neurodegenerative disease or damage.

The methods involve applying an effective amount of light energy to the patient's head. By applying light energy, portions of the brain are activated. To "activate" as used herein means to change the electrical state of cells or tissues, in a positive or negative direction. That is, activation can refer to both increasing and decreasing electric current, voltage, potential or magnetic fields of cells or tissues. The activation may, in turn, open or close ion channels, cause the transition of one molecule into another state, convert biological molecules from a passive state to an active state or vice versa, and thereby modulate brain function. The activation may be temporary, reversible or permanent.

The activation may be measured by direct methods such as electroencephalography, either on the scalp or intracranially, both referred to herein as EEG unless expressly differentiated. The activation may be measured by indirect methods such as SPECT, fMRI, PET, NIRS, or a combination of direct and indirect methods. The activation may be more clearly quantified by combining measurements of brain activation with other anatomical information, such as electric tomography and electrooculogram.

The following table sets forth some of the locations to be treated for specific diseases:

| Disease | Main location to be treated on the human brain |
|---|---|
| Alzheimer's | frontal cortex, temporal lobe and base of brain |
| Amyotrophic lateral sclerosis ("ALS") | motor cortex |
| Autism spectrum disorder | frontal lobes, temporal lobe and base of brain |
| Epileptic seizures | cortex |
| Huntington's disease | basal ganglia |
| Parkinson's disease | midbrain |
| Pick's disease and other fronto-temporal dementias | frontal lobe |

Some diseases are not area-specific. That is, some diseases are not necessarily due to a specific damaged area of the brain, instead occurring throughout the brain, or at a different location for each patient, such as Creutzfeldt-Jakob disease, hypothyroidism, Lewy body dementia, normal pressure hydrocephalus, tauopathies, and vascular dementia. For example, with vascular dementia, blood vessels through the brain may be affected, some more than others. For these maladies the light is applied all over the head. For an inflammation-based disease such as Parkinson's, the more areas of the brain that can be treated the more effective treatment is. In fact, due to the systemic effects of applying light anywhere to the brain, the application of light on any area of the skull will work on any malady to some degree, and application to multiple areas is often beneficial. In one embodiment the treatment is applied to a specific hemisphere of the brain. For some diseases the treatment is applied to acupuncture points on the brain.

In one embodiment, the laser energy is applied to area above the glabellomeatal and infraorbitomeatal lines. See FIG. 7. The infraorbitomeatal line is used as the zero plane in computed tomography and is thus known to persons skilled in the art of brain radiology. The infraorbitomeatal line is a line drawn from the inferior margin of the orbit to the auricular point (center of the orifice of the external acoustic meatus) and extending backward to the center of the occipital bone. The glabellomeatal line is also used in computed tomography and thus is also known to persons skilled in the art of brain radiology. The glabellomeatal line is an imaginary line that extends from the *glabella* to the center of the external auditory meatus. FIG. 7 illustrates the two lines and the shaded area is the area above the glabellomeatal and infraorbitomeatal lines.

In other embodiments, treatment can be solely above the glabellomeatal and infraorbitomeatal lines, both above and below glabellomeatal and infraorbitomeatal lines, or solely below glabellomeatal and infraorbitomeatal lines.

Another variable in the light treatment parameters is the intensity or fluence of the light energy. Bio stimulation occurs with the application of between 0.001 to 5 joules of energy. For example, U.S. Pat. No. 7,118,588, incorporated here by reference, discloses a line generator for laser light application. At 4 inches away from the scalp, the 70 degree line generator as disclosed therein creates a projected beam that is 14 cm long and 3 mm wide for a total beam area of 420 mm$^2$. The size of each treatment area is the same as the beam profile because the diode is not moved during procedure administration. Given a 600 second treatment time with a 7.5 mW laser, the total energy each produced by each independent laser diode is 4.5 joules per laser. The fluence per laser is calculated as 0.011 J/cm$^2$. Using a laser with 5 independent laser diodes, as shown in FIG. 1, each laser diode treats a different (separate) areas of the head, so the fluence remains the same (unchanged) at 0.011 joules; however, the total energy delivered to the subject per 10-minute procedure administration across all 5 laser diodes and respective treatment areas combined is 22.5 joules.

Preferably the power density at the treated surface is less than 10 mW/cm$^2$. Note that this is the surface power density, not the subsurface power density. In one embodiment, the surface power density is about 1.78 mW/cm$^2$.

Advantageously, these methods use low-level light therapy which has an energy dose rate that causes no detectable temperature rise of the treated tissue immediately upon treatment or over time, and no macroscopically visible changes. This holds true at the treated surface, the treated tissue, tissue within the treatment area, around the treatment area, or any intervening or targeted tissue of the patient's body. No cooling or blanching of tissue is needed to maintain the tissue temperature, nor is any diffusion of the treatment energy needed to maintain tissue temperature. Consequently, the light energy is applied directly to the patient, with no intervening device or structure between where the laser light exits the laser device and the patient, making for a relatively simple and efficient treatment process. In other words, no element exists between the light once it is emitted from the laser device until it impinges on the patient, so there is nothing in the line of emission that would change the direction of the emission, stop it, or modulate it.

The laser energy can be applied to the patient using a variety of laser devices, such as a hand-held laser device, a full-body laser scanner, a wall-mounted laser device, or a stand-alone laser device. Handheld lasers are described in U.S. Pat. Nos. 6,013,096 and 6,746,473, which are incorporated herein by reference. A full-body laser scanner is described in U.S. Pat. No. 8,439,959, incorporated herein by reference. Wall-mount and stand-alone lasers are described in U.S. Pat. No. 7,947,067, and incorporated herein by reference.

In a preferred embodiment, the light is emitted in a line and the line is waved manually across a person's skull in the desired area in a continuous, sweeping manner. In another embodiment the shape of the beam spot on the treated area is an apparent circle, which is actually a rotating diameter by a line of light. U.S. Pat. No. 7,922,751, incorporated herein by reference, discloses a device to sweep such a circular beam spot. The device disclosed in that patent can be programmed to move the scanning head in a manner to achieve any desired shape of a treatment zone on the head of a patient. A sample selection of available scan patterns is shown in that patent at FIGS. 8a-h.

Activation Example

A 28-year old patient with a healthy brain was treated in a room with controlled temperature from 24 to 26 C, noise attenuation, and dimmed lights. Twenty minutes of EEG were recorded immediately before treatment. Laser light was applied for 10 minutes to the patient's skull through his hair using a hand-held laser. The light energy was applied by the Erchonia® EAL Laser, a hand-held laser with two 640 nm nominal semiconductor laser diodes at pulse frequencies of 4 Hz, 12 Hz, 33 Hz, and 60 Hz. The light energy was applied to the frontal lobe, occiput, cerebellum, cortex, and brain stem using a sweeping motion continuously during treatment. Twenty minutes of EEG were recorded immediately after treatment.

The data were assessed using quantitative EEG and quantitative electric tomography ("QEEGT"). QEEGT is a technique that combines anatomical information of the brain by MRI with EEG patterns, to estimate the sources of the EEG within the brain. The EEG was recorded using nineteen monopolar derivations of the International 10-20 System (FP1, FP2, F3, F4, C3, C4, P3, P4, O1, O2, F7, F8, T3, T4, T5, T6, Fz, Cz, Pz) with linked earlobes as a reference. Eye movement artifacts were monitored by use of the electrooculogram (EOG). The data acquisition was performed using a MEDICID-07 System (Neuronic, S.A.). After visual editing to remove artifacts, 48 artifact-free samples were selected, each 2.5 seconds long, for each experimental condition, and were transformed using the FFT to the frequency domain, yielding a power spectrum from 0.78 to 70 Hz with a sampling frequency of 0.39 Hz (178 frequencies), with a 60 Hz notch filter.

FIG. 2 shows images of the QEEGT of the patient's brain, before and after treatment. After treatment the patient showed increased brain activity within the gamma band. Arrows 71a, 71b, and 71c point to the portions of the brain having increased gamma band activity. A decrease in gamma-band activity is known to be associated with cognitive decline, and increasing the gamma band activation may help maintain a healthy brain and delay onset of cognitive decline.

Alzheimer's Example

In one example light therapy is applied to patients with mild to moderate Alzheimer's disease improve their memory, thinking and behaviors. The light-emitting device is a mains powered variable hertz laser device made up of five independent red laser diodes mounted in scanner devices and positioned equidistant from each other. Each scanner emits 7.5 milliwatts (m)±1.0 mW 640 nanometers (nm) with a tolerance of ±10 nm of red laser light.

The laser energy is administered to each patient's frontal cortex, temporal regions and base of the skull 8 times across 4 consecutive weeks, 2 times each week, for 10 minutes of treatment time during each of 8 treatments. The total energy delivered to the patient per procedure administration is 22.5 joules. The patient's frontal cortex, temporal regions and the base of the skull are lazed equally in a continuous sweeping motion continuously during the 10-minute treatment session using pulse frequencies of 8 Hz, 53 Hz, 73 Hz and 101 Hz. The laser energy is applied four inches from the skin surface, and the laser light is directed perpendicular to the plane of the skin ensuring that the beam is penetrating perpendicular to the skin.

The treatment for patients with autism preferably utilizes red laser energy at 635 nm±10 nm, from one or more 7.5 mW±1.0 mW semiconductor laser diodes. Each treatment uses one or more pulse frequencies at 8 Hz, 53 Hz, 73 Hz and 101 Hz. The length of each treatment is 2-12 minutes, and preferably 5 or 10 minutes. The number of treatments varies, depending on that patient's size, weight, age, and severity of the autism symptoms. Patients may see improvement after a single treatment, but typically see improvement after 6 treatments. Treatments may be given periodically or as needed after the initial set of treatments to maintain or further improve the symptoms. For some autism treatments protocols, it is desirable to have at least one treatment area above glabellomeatal and infraorbitomeatal lines.

Autism Example #1

Children exhibiting autistic behaviors are treated with low-level laser by scanning each patient's frontal cortex, temporal area and the base of the brain for 10 minutes, twice weekly, 3-4 days apart, for three consecutive weeks, for a total of 6 treatments. The patient's frontal cortex, temporal area and the base of the brain are lazed equally in a continuous sweeping motion continuously during the 10-minute treatment session using pulse frequencies of 8 Hz, 53 Hz, 73 Hz and 101 Hz. The light-emitting device used comprised a hand-held laser device with two 7 mW red semiconductor laser diodes emitting a line of red laser light at a wavelength of 635 nm±5 nm. Changes in behavior are measured using the Aberrant Behavior Checklist ("ABC"). Significant improvements are achieved in all 5 ABC Subscales and the ABC global score. No adverse events occurred.

Autism Example #2

Children exhibiting autistic behaviors are treated with low-level laser by scanning each patient's temporal areas and the base of the brain for 5 minutes, twice weekly, 3-4 days apart, for four consecutive weeks, for a total of 8 treatments. The patient's temporal regions and the base of the brain are lazed equally in a continuous sweeping motion continuously during the 5-minute treatment session using pulse frequencies of 8 Hz, 53 Hz, 73 Hz and 101 Hz. The light-emitting device used comprises a hand-held laser device with two 7 mW red semiconductor laser diodes emitting a line of red laser light at a wavelength of 635 nm±5 nm.

Autism Example #3

A patient suffering from autism symptoms is treated with a 15 mW hand-held laser device, emitting a line of red laser light at a wavelength of 635 nm±5 nm from semiconductor laser diodes. The line of laser light is manually scanned on the front of the patient's head near the frontal lobes using one or more pulse frequencies of 8 Hz, 53 Hz, 73 Hz and 101 Hz. The patient is treated for 5 minutes in each treatment, having two treatments per week for four weeks.

Autism Example #4

A patient suffering from autism symptoms is treated with a 15 mW hand-held laser device, emitting a line of red laser light at a wavelength of 635 nm±5 nm from semiconductor laser diodes. The line of laser light is manually scanned on the front of the patient's head near the frontal lobes and on the patient's head near the temporal lobes. The patient is treated for 5 minutes in each treatment, twice weekly, 3-4 days apart, for four consecutive weeks, for a total of 8 treatments.

Autism Example #5

A patient suffering from autism symptoms is treated with hand-held laser device that has two 7.5 mW semiconductor laser diodes, emitting lines of red laser light at a wavelength of 635 nm±5 nm. The laser light is manually scanned on the front of the patient's head near the frontal lobes, on the patient's head near the temporal lobes, and on the patient's head near the base of the brain. The patient is treated for 5 minutes in each treatment, having treatments 3-4 times per week for four weeks.

Autism Example #6

A patient suffering from autism symptoms is treated with hand-held laser device that has two 7 mW semiconductor laser diodes, emitting lines of laser light at a wavelength of 635 nm nominal. The line of laser light is manually scanned on the patient's head near the temporal lobes, and on the patient's head near the base of the brain, about 4" from the skin, using one or more pulse frequencies of 8 Hz, 53 Hz, 73 Hz and 101 Hz. The patient is treated for 5 minutes in each treatment, resulting in 2.10 J applied per treatment. The patient is treated 2 times per week, 3-4 days apart, for 4 weeks.

Heart Rate Variability Example

In another embodiment, light energy is applied to the patient to increase heart rate variability (HRV) by applying light energy. The applied energy has a wavelength in the range of about 400-700 nm, with the desired wavelength within the spread from nominal. In some embodiments multiple wavelengths are used, either in series, alternately, or simultaneously, and preferably include 635 nm nominal. For example, in a preferred embodiment, both 400 nm and 635 nm light are applied simultaneously. The light can be from any source including light-emitting diodes, hard-wired lasers, or laser diodes, but preferably is from a semiconductor laser diode such as Gallium Aluminum Arsenide (GaAlAs) laser diodes, emitting red laser light at 635 nm nominal. Commercial semiconductor laser diodes have a spread of ±10 nm from nominal so the light applied is within the spread from nominal.

The applied energy is low-level, typically from emitters of less than 1 W. The total energy applied ranges from 0.001 to 10 joules. The applied light may be continuous or pulsed in a range of 1-10,000 hertz. This low-level light therapy has an energy dose rate that causes no detectable temperature rise of the treated tissue and no macroscopically visible changes in tissue structure. Consequently, the tissue impinged by the light is not heated and is not damaged.

Figure 10:
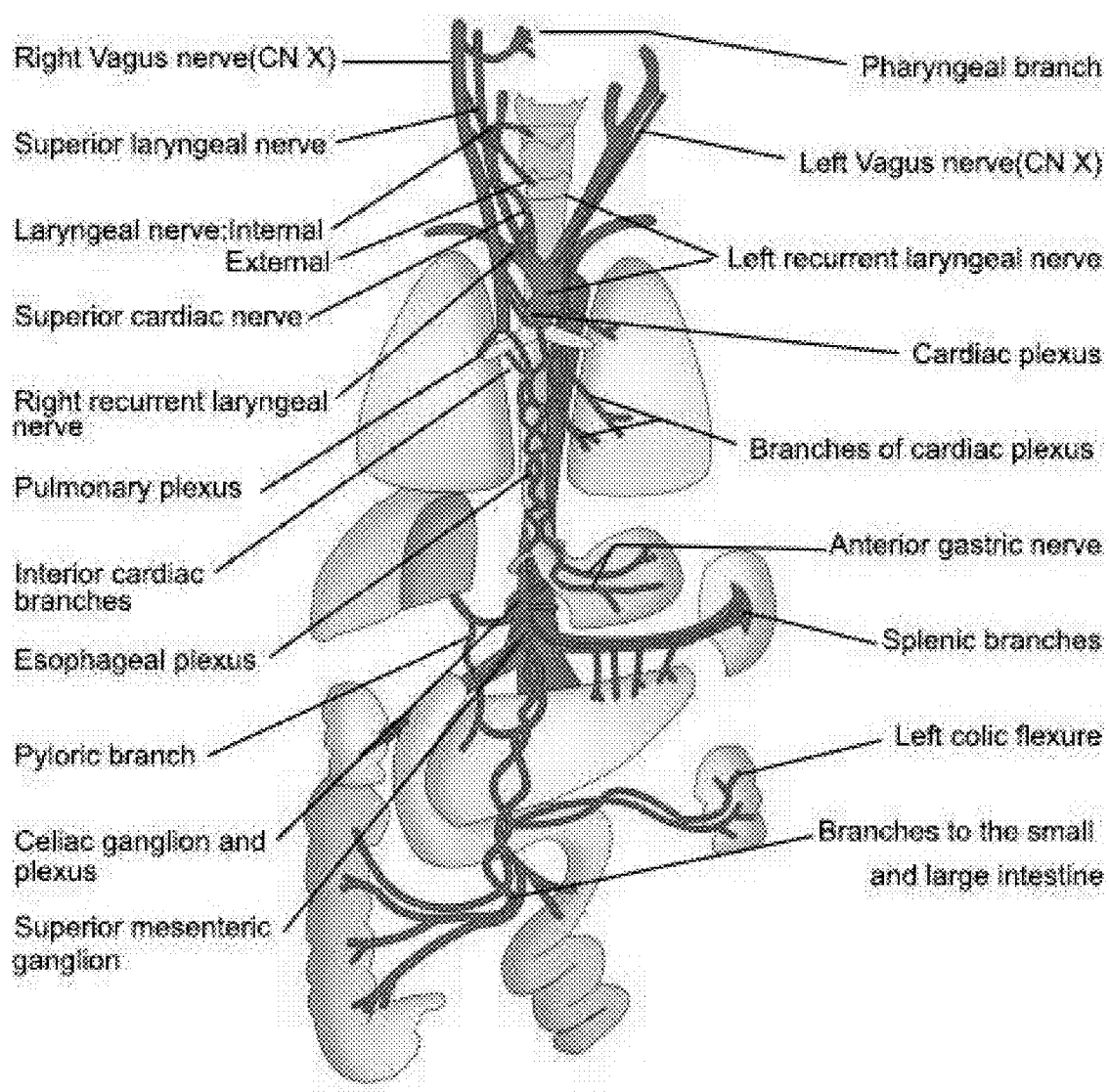
FIG. 10 is a schematic illustration of the vagus nerve, its general location and its connection to major organs.

Preferably the light energy 14 is applied to the patient's neck 8 where branches of the vagus nerve 7 are close to the surface. See FIG. 10. Depending on the patient, then, the light energy can be applied to the right, left, front, or back of the patient's neck, or a combination thereof, to assure that energy is reaching the vagus nerve.

Analysis of beat-to-beat variability is a simple, non-invasive measurement, which may be collected using electrocardiogram or plethysmograph.

In one embodiment, a patient's HRV was measured pre-treatment. Laser light energy at 635 nm was applied for 5 minutes externally to the left side of the patient's neck in a sweeping back-and-forth motion using a hand-held laser device 12. See FIG. 8. The patient's HRV was measured post-treatment and found to have increased.

In another embodiment, a patient's HRV was measured pre-treatment. Laser light energy at 400 nm was applied for 5 minutes externally to the left side of the patient's neck in a sweeping back-and-forth motion using a hand-held laser device 12. See FIG. 9. The patient's HRV was measured post-treatment and found to have increased.

In yet another embodiment, a patient's HRV was measured pre-treatment. Laser light energy at 635 nm and at 400 nm was applied simultaneously for 5 minutes externally to the left side of the patient's neck in a sweeping back-and-forth motion using a hand-held laser device 12. The patient's HRV was measured post-treatment and found to have increased.

The application of light energy may be accompanied by spinal manipulation or massage therapy, which assists in reducing the pressure and tension the musculoskeletal system places upon the vagus nerve and which may also alter HRV.

Vagus nerve stimulation by the application of light energy may be used treat and prevent cardiovascular disease, cancer, chronic obstructive pulmonary disease, diabetes, stroke, myocardial infarction, anxiety disorders, obesity, alcohol addiction, chronic heart failure, prevention of arrhythmias that can cause sudden cardiac death, autoimmune disorders, and several chronic pain conditions including migraines and fibromyalgia. Vagus nerve stimulation by the application of light energy may also be used treat and prevent neurodevelopmental disorders, including epilepsy and autism spectrum disorders.

In another application, the methods herein treat opioid use disorder through substituting light therapy for opioid use (weaning) and effecting brain neuromodulation to reduce opioid withdrawal symptoms, including pain. A typical patient is an adult undergoing opioid-use weaning during the acute physical withdrawal phase who meets the DSM-IV criteria for opioid dependence, has a positive urine toxicology screen for opioids, and a Clinical Opioid Withdrawal Score (COWS) of 5 or greater.

Opioid Use Disorder Example

Erchonia Corporation recently completed a double-blind, placebo-controlled randomized clinical evaluation of Erchonia LLLT applied to the base and temporal regions of the brain of children and adolescents with autistic disorder. Light energy in the range of range from about 400-760 nm was applied externally to a patient's head to stimulate different neurological pathways, reduce inflammation and stimulate mitochondria function in the brain. In a preferred embodiment, the applied light energy is applied with a pulse frequency or frequencies that mimic healthy brain function of alpha, beta, delta, and theta waves. Furthermore, the treatment was enhanced by activating the cranial nerves while the light is applied.

The results showed an improvement in irritability. Primary outcome of change in ABC Irritability Subscale score was −13.55 for active subjects and +0.32 for placebos, the difference exceeding the pre-established success criteria of −8.5 by 5.32 points. 80% of active subjects met the Positive Responder Rate of both a ≥25% reduction in ABC Irritability Subscale score and CGI-C rating of 1 (very much improved) or 2 (much improved) at endpoint, compared with no (0%) placebos. All measures continued to demonstrate progressive improvement for test subjects through 6 months follow up, some to near-normal levels. No adverse events occurred.

To treat opioid use disorder, low-level laser energy is applied externally to a patient at the vagus nerve, and optionally the frontal and temporal lobes for pain management. In one embodiment, the laser energy is applied to the vagus nerve and above the glabellomeatal and infraorbitomeatal lines. The applied energy is in the range of about 400-700 nm, and is preferably 635 nm nominal, although wavelengths below 400 nm and above 700 nm may suffice.

In one example, the laser energy is administered to the patient's vagus nerve for 10 minutes of treatment time 2 times each week, for 4 weeks. The total energy delivered to the patient per procedure administration is 22.5 joules. The laser energy is applied in a continuous sweeping motion continuously during the 10-minute treatment session. In one embodiment, the laser energy is applied using pulse frequencies of 8 Hz, 53 Hz, 73 Hz and 101 Hz.

While there has been illustrated and described what is at present considered to be the preferred embodiments of the present invention, it will be understood by those skilled in the art that various changes and modifications may be made and equivalents may be substituted for elements thereof without departing from the true scope of the invention. Therefore, it is intended that this invention not be limited to the particular embodiments disclosed, but that the invention will include all embodiments falling within the scope of the appended claims.

The invention claimed is:

1. A method of activating a desired portion of a patient's healthy brain comprising applying an effective amount of light energy to the patient's skull above the glabellomeatal and infraorbitomeatal lines and at a pulse frequency of brain waves emanating from a healthy brain, wherein:
   a. the light energy is applied by a device disposed entirely externally to the patient;
   b. the direct application of light energy causes no detectable temperature rise of the treated location; and
   c. the light energy has a wavelength above 400 nm and below infrared wavelengths wherein the light energy is applied in a continuous sweeping motion.

* * * * *